United States Patent [19]

Fletcher et al.

[11] 4,450,093

[45] May 22, 1984

[54] INDOLIZINONE DYES AND COMPOSITIONS, ELEMENTS AND METHODS USING SAME

[75] Inventors: George L. Fletcher, Pittsford; Donald H. Wadsworth, Rochester, both of N.Y.

[73] Assignee: Eastman Kodak Company, Rochester, N.Y.

[21] Appl. No.: 443,788

[22] Filed: Nov. 22, 1982

Related U.S. Application Data

[62] Division of Ser. No. 278,023, Jun. 29, 1981, Pat. No. 4,373,021.

[51] Int. Cl.$^3$ .......................... C09K 3/00; G03C 5/24
[52] U.S. Cl. .................................... 252/182; 430/374; 430/541; 430/495; 544/216; 544/353
[58] Field of Search ............... 252/182; 430/374, 541, 430/495; 544/216, 353

[56] References Cited

U.S. PATENT DOCUMENTS

4,128,422 12/1978 Fletcher et al. ................... 430/290

OTHER PUBLICATIONS

Canadian J. of Chem., vol. 49, pp. 1165–1175, (1971).

*Primary Examiner*—Won H. Louie, Jr.
*Attorney, Agent, or Firm*—Dana M. Schmidt

[57] ABSTRACT

There are disclosed dyes, compositions, imaging elements, and methods of forming images, wherein cyclopropenones are reacted with di- or tri-halogenated compounds in the presence of pyridine to form said dyes. In areas exposed to activating radiation, the cyclopropenone decomposes and prevents the dye reaction from occurring.

6 Claims, No Drawings

INDOLIZINONE DYES AND COMPOSITIONS, ELEMENTS AND METHODS USING SAME

This is a division of application Ser. No. 278,023, filed June 29, 1981, U.S. Pat. No. 4,373,021.

FIELD OF THE INVENTION

This invention relates to dyes and compositions useful in imaging elements and methods, as well as to non-image dye applications.

BACKGROUND OF THE INVENTION

Prior to this invention, co-workers Fletcher, Wadsworth and Bender developed a class of dyes useful for, among other things, imaging elements and methods wherein a mono-halogenated compound is reacted with the oxidized form of the reaction product of a pyridine and a cyclopropenone. The oxidation of the reaction product in this development by Fletcher et al preferably features the use of oxygen from air. Although such dyes, imaging elements and methods are highly useful, it would be advantageous to develop a dye reaction that is independent of oxygen. In such a case imaging elements could be constructed with overcoats that provide a variety of functions without regard to whether the overcoats also are readily permeable to air or other sources of oxygen.

The above-noted development is described and claimed in commonly owned U.S. application Ser. Nos. 278,022 & 278,013, filed on June 29, 1981 & June 29, 1981 by Fletcher, Bender & Wadsworth, entitled "Oxo-Indolizine and Oxo-Indolizinium Dyes and Processes For Their Preparation" and "Photographic Materials and Processes Comprising Oxo-Indolizine and Oxo-Indolizinium Compounds".

SUMMARY OF THE INVENTION

The problems noted in the preceding "Background" are overcome by compositions that comprise a cyclopropenone and a compound substituted with reactive multiple halogens, that is, two or three halogens that are bonded to an active carbon atom and are reactable in pyridine with the cyclopropenone to form a dye.

Thus, in accordance with one aspect of the invention, there are advantageously featured a dye-forming composition, element, and imaging method which do not require the presence of oxygen for the dye reaction.

It is a related advantageous feature of the invention that such dye-forming compositions, elements and imaging methods tolerate an extensive variety of overcoats without regard to whether such overcoats are oxygen permeable.

More specifically, there is provided a composition reactable with pyridine to form a dye, the composition comprising a cyclopropenone having the structural formula

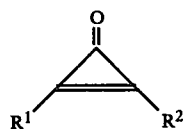

and either a compound of the structural formula

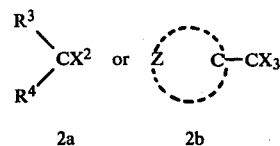

wherein $R^1$ and $R^2$ are individually alkyl of 1 to 5 carbon atoms, aryl of 6 to 10 nuclear carbon atoms, or a heterocyclic group of from 5 to 6 nuclear atoms selected from the group consisting of carbon, oxygen, and sulfur;

$R^3$ is an organic moiety such that, when 1 mmole of compound 2a is added to 5 g of pyridine as solvent, and 0.2 mmole of the noted cyclopropenone, and heated to a temperature of about 80° C. for up to 1 hour, a dye is formed having an optical density of at least 0.5 when measured at $\lambda_{max}$ in a cell having a 1 mm path length;

$R^4$ is hydrogen, alkyl of 1 to 5 carbon atoms, halogen, or one of the group of $R^3$;

X is halogen;

and Z represents the non-metallic atoms necessary to complete one, two or three fused rings of 5 to 14 nuclear atoms selected from the group consisting of carbon and nitrogen.

Alternatively, $R^3$ is selected from the group consisting of aryl of 6 to 10 nuclear carbon atoms and bearing a bathochromic substituent; nitro; carbonyl; amide; sulfonyl; and cyano. If the composition is on a support to form an imaging element, $R^3$ can be described as an organic moiety that renders $X_2$ sufficiently reactive, when the composition is coated with about 0.05 mmole/dm² of the cyclopropenone and about 0.1 mmole/dm² of compound 2a, and excess pyridine at a temperature of about 80° C. is added, to yield a dye having an optical density measured at $\lambda_{max}$, of at least 0.5.

Such an imaging element is useful in an imaging method comprising the steps of (a) imagewise exposing the element to activating radiation; and (b) developing the exposed element by adding excess pyridine to the composition.

Other features of the invention will become apparent upon reference to the following description of the preferred embodiments.

DESCRIPTION OF THE PREFERRED EMBODIMENTS

It has been discovered that the dyes and methods of Fletcher, Wadsworth, and Bender described above can be improved so that an oxygen-containing atmosphere is not required for dye formation. The improvement resides in the use of a compound that is multi-halogenated at at least of the active carbon atoms. Such compounds do not require the presence of additional oxidizing agents in order to form a dye when combined with a cyclopropenone and excess pyridine.

The carbon to which the halogens are bonded is rendered active, when compound 2a is used, by an additional substituent on that carbon, or on adjacent carbons, that causes the halogens to react with the cyclopropenone-pyridine reaction product in an amount sufficient to form a dye having an optical density, measured at $\lambda_{max}$, of at least 0.5.

Such a dye and method of forming it are particularly useful in obtaining an imaging element and composition wherein a latent image is formed by imagewise destroying some of the cyclopropenone. Thereafter, sufficient pyridine is added to the composition or element to cause dye formation in the unexposed portions. Because the dye reaction proceeds independently of oxygen, optional overcoats are useful with the imaging elements featuring this invention, whether or not the overcoats are permeable to oxygen.

The cyclopropenone of the composition preferably has the structure 1 above. Useful examples of $R^1$ and $R^2$ include alkyl such as methyl, ethyl, propyl and isopropyl; aryl such as phenyl and naphthyl; and heterocyclics such as furans, pyrans, and thiophenes. As used herein for $R^1$ and $R^2$, "alkyl" and "aryl" include substituted alkyl and substituted aryl. Examples of substituted alkyl include 1-phenyl-2-benzoylethyl. Substituted aryl includes alkoxy-, nitro-, cyano- and alkylphenyl, for example, 4-methoxyphenyl and anisyl. As used herein, "anisyl" is understood to mean a mixture of 4- and 2-methoxyphenyl so that one of $R^1$ and $R^2$ is one and the other of $R^1$ and $R^2$ is the other.

In accordance with one aspect of the invention, the compound added to the cyclopropenone for the dye reaction that takes place in the presence of pyridine, is a multi-halogenated compound having the structure 2a or 2b of the Summary.

If compound 2a is used, $R^3$ is selected from any organic moiety that renders the $-X_2$ group sufficiently reactive with said pyridine and said cyclopropenone to form a dye with an optical density of at least 0.5.

A simplified solution test for determining organic moieties that have such reactivity is as follows: About 0.2 mmoles of the cyclopropenone is added to 5 g of pyridine as a solvent, and about 1 mmole of the compound 2a the reactivity of which is under consideration. The composition so obtained is heated to a temperature of about 80° C. for a length of time of up to 1 hour. If a dye has formed producing an optical density of at least 0.5 when measured at its $\lambda_{max}$ in a 1 mm path length cell, the $R^3$ moiety is sufficiently reactive.

Alternatively, the reactivity of the $R^3$ moiety can be determined in the format of a coating on a support such as would be useful in an imaging element. The composition is prepared as for the simplified solution test described in the previous paragraph, except that the amounts are selected so that when dried, the coating has about 0.05 mmoles/dm² of the cyclopropenone, about 0.1 mmoles/dm² of the compound 2a, and optionally a binder. (The ratio of compound 2a to cyclopropenone is reduced compared to the simplified test of the previous paragraph, because a coated element gives better results when the total amount of ingredients is reduced.) Excess pyridine heated to 80° C. is added, and the optical density of the dye produced in the coating is measured at $\lambda_{max}$. If the density is at least 0.5, then the $R^3$ group is sufficiently reactive. Such optical density corresponds to the $D_{max}$ density values that are produced when an imaging element of the invention containing the composition is fully exposed imagewise, and developed with pyridine.

Specifically useful examples of $R^3$ include nitro; carbonyl; amide; sulfonyl; cyano; and aryl of from 6 to 10 nuclear carbon atoms, for example, phenyl and naphthyl, provided the aryl bears a bathochromic substituent. As used herein for $R^3$, "sulfonyl" and "carbonyl" are understood as including substituted or unsubstituted sulfonyl and carbonyl, respectively, of which the substituents phenyl, amino, methyl, and 2-benzothiazolyl are particularly useful. Thus, both ketones and aldehydes are available as $R^3$ moieties. Also as used herein, a "bathochromic substituent" or "bathochromic moiety" is one which completes the formation of the chromophore by providing for the delocalization of electron density so that the electrons are distributed more uniformly, leading to an absorption of visible light. Useful bathochromic substituents for the aryl of compound 2a include nitro, acryloyl, aminocarbonyl, cyano, sulfonyl, and carboalkoxy such as carboethoxy.

Selection of $R^3$ as noted above allows $R^4$ to be selected with greater freedom. That is, useful groups for $R^4$ include each of those substituents useful as $R^3$, as well as hydrogen, halogen such as chlorine, bromine, and the like; and alkyl of 1 to 5 carbon atoms, such as methyl, ethyl, butyl and pentyl. As used herein, "alkyl" for $R^4$ includes substituted alkyl. Useful substituents for the substituted alkyl include aryl such as phenyl, =O, and benzoyl.

If compound 2b is used, examples of the heterocyclic ring completed by the atoms of Z include azine rings such as triazine and quinoxaline, as well as rings containing a single nitrogen atom only, such as quinoline and acridine rings. Highly preferred examples of compound 2b include 2,4-bis(tribromo- and 2,4-bis(trichloromethyl)-6-methyl-1,3,5-s-triazine, 2-tribromo and 2-trichloromethylquinoxaline, and 2-tribromomethylquinoline.

Particularly preferred dyes of the invention are those having the structural formula

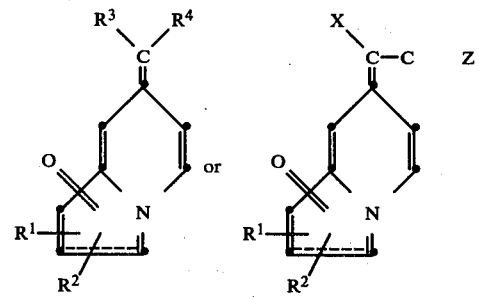

wherein, $R^1$-$R^4$, X and Z are as defined above. For example, highly preferred dyes are those having a Z group that forms an azine compound such as quinoxaline or a trihalomethyl substituted s-triazine, and ring compounds containing a single nitrogen atom.

The following table is a list of particularly preferred compounds 2a or 2b, and the dyes and colors they produce when reacted with pyridine and the noted cyclopropenone. The color and $\lambda_{max}$ values were obtained from a methylene chloride solution at a concentration of 0.02 weight percent.

TABLE I

| Compound 2a or 2b | $R^1$ & $R^2$ of Cyclopropenone | Dye Produced |
|---|---|---|
| 4,4-dibromo-1,3-diphenyl-4-nitro-1-butanone | 4-methoxyphenyl | 1-oxo-2,3-di(4-methoxyphenyl)-7-(2,4-diphenyl-1-nitro-4-oxobutylidene)-7H—indolizine; $\lambda_{max}$ = 610 nm; color = blue |
| 1,1-dibromo-1-phenyl- | 4-methoxyphenyl | 1-oxo-2,3-di(4-methoxyphenyl)-7-(1-aminocarbonyl-1- |

TABLE I-continued

| Compound 2a or 2b | R$^1$ & R$^2$ of Cyclopropenone | Dye Produced |
|---|---|---|
| sulfonylacetamide | | benzenesulfonylmethylidene)-7H—indolizine; $\lambda_{max}$ = 570 nm; color = purple |
| 2-tribromomethyl-quinoline | 4-methoxyphenyl | 7-[1-bromo-1-(2-quinolinyl)methylidene]-2,3-(4-methoxyphenyl)-1(7H)—indolizinone; $\lambda_{max}$ = 600 nm; color = blue |
| 2,4-bis(tribromomethyl)-6-methyl-s-triazine | n-propyl | 7-[1-bromo-1-(4-tribromomethyl-6-methyl-1,3,5-triazinyl)methylidene]-2,3-di-n-propyl-1(7H)—indolizinone; $\lambda_{max}$ = 600 nm; color = blue |
| trichloroacetonitrile | 4-methoxyphenyl | 7-(1-chloro-1-cyanomethylidene)-2,3-di(4-methoxyphenyl)-1(7H)—indolizinone; $\lambda_{max}$ = 580; color = purple |
| ethyl 4-dibromomethyl-benzoate | 4-methoxyphenyl | 1-oxo-2,3-di(4-methoxyphenyl)-7-[(4-carboethoxyphenyl)methylidene]-7H—indolizine; $\lambda_{max}$ = 615 nm; color = blue |
| 2-tribromomethylsulfonyl-benzothiazole | 4-methoxyphenyl | 1-oxo-2,3-di(4-methoxyphenyl)-7-[(2-benzothiazolylsulfonyl)bromomethylidene]-7H—indolizine; $\lambda_{max}$ = 585 nm; color = purple |
| 2,6-trichloromethyl-4-(1-naphthyl)-s-triazine | 4-methoxyphenyl | 1-oxo-2,3-di(4-methoxyphenyl)-7-{1-chloro-1-{2-[4-(1-naphthyl)-6-trichloromethyl-1,3,5-triazinyl]}-methylidene}-7H—indolizine; $\lambda_{max}$ = 640 nm; color = blue-green |
| 2-tribromomethyl-quinoxaline | phenyl | 3-oxo-1,2-diphenyl-7-[bromo(2-quinoxalinyl)methylidene]-7H—indolizine; $\lambda_{max}$ = 500 nm; color = red |
| 2-tribromomethyl-quinoline | phenyl | 1-oxo-2,3-diphenyl-7-[bromo(2-quinolinyl)methylidene]-7H—indolizine; $\lambda_{max}$ = 590 nm; color = blue |
| 2-tribromomethyl-quinoline | phenyl | 3-oxo-1,2-diphenyl-7-[bromo-(2-quinolinyl)methylidene]-7H—indolizine; $\lambda_{max}$ = 480 nm; color = orange |
| 2,4-bis(tribromomethyl)-6-methyl-s-triazine | 4-methoxyphenyl | 1-oxo-2,3-di(4-methoxyphenyl)-7-{bromo-[2-(4-methyl-6-tribromomethyl-1,3,5-triazinyl)]methylidene}-7H—indolizine; $\lambda_{max}$ = 630 nm; color = blue-green |
| 1,1-dibromo-1-phenyl-sulfonylacetamide | n-propyl | 7-(1-aminocarbonyl-1-benzenesulfonylmethylidene)-2,3-di-n-propyl-1(7H)—oxoindolizinone; $\lambda_{max}$ = 525–550 nm; color = magenta |
| 1,1-dibromo-1-phenyl-sulfonylacetamide | phenyl | 7-(1-aminocarbonyl-1-benzenesulfonylmethylidene)-2,3-diphenyl-1(7H)—indolizinone; $\lambda_{max}$ = 565 nm; color = magenta |
| 2-tribromomethyl-quinoxaline | phenyl | 1-oxo-2,3-diphenyl-7-[bromo(2-quinoxalinyl)-methylidene]-7H—indolizine; $\lambda_{max}$ = 600 nm; color = blue |
| trichloroacetonitrile | phenyl | 7-(1-chloro-1-cyanomethylidene)-2,3-diphenyl)-1(7H)—indolizinone; $\lambda_{max}$ = 570; color = purple |
| tribromoacetaldehyde | phenyl | 7-(1-bromo-1-formylmethylidene)-2,3-diphenyl)-1(7H)—indolizinone; $\lambda_{max}$ = 590; color = blue |
| ethyl 4-dibromomethyl-benzoate | p-methoxyphenyl | 7-[1-(4-carboethoxyphenyl)methylidene]-2,3-di-(4-methoxyphenyl)-1(7H)indolizinone; $\lambda_{max}$ = 615; color = green |
| dibromomalonitrile | phenyl | 7-(1,1-dicyanomethylidene-2,3-diphenyl-1(7H)—indolizinone; $\lambda_{max}$ = 555, 590; color = purple |
| 2-4-tribromomethyl-6-methyl-1,3,5-triazine | phenyl | 7-{1-bromo-1-[2-(4-methyl-6-tribromomethyl-1,3,5-azinyl)]methylidene}-2,3-diphenyl-1(7H)—indolizinone; $\lambda_{max}$ = 630 nm; color = blue-green |
| dichloromalonoitrile | 4-methoxyphenyl | 7-(1,1-dicyanomethylidene)-2,3-di-(4-methoxyphenyl)-1(7H)—indolizinone; $\lambda_{max}$ = 565 nm; color = purple |

In addition to the above, the following mixed dyes are formed using dianisylcyclopropenone together with one of the compounds 2a or 2b of Table I. They are mixed dyes, because about 50% of the resultant product has the p-methoxyphenyl substituent attached alpha to the nitrogen atom of the indolizinone structure, and about 50% of the resultant product has the p-methoxyphenyl substituent attached beta to the nitrogen atom:

1-oxo-2,3-dianisyl-7-(2,4-diphenyl-1-nitro-4-oxobutylidene)-7H-indolizine;

1-oxo-2,3-dianisyl-7-(1-aminocarbonyl-1-benzenesulfonylmethylidene)-7H-indolizine;

7-(1-chloro-1-cyanomethylidene)-2,3-dianisyl-1(7H)-indolizinone;

1-oxo-2,3-dianisyl-7-[(4-carboethoxyphenyl)methylidene]-7H-indolizine;

1-oxo-2,3-dianisyl-7-[(2-benzothiazolylsulfonyl)-bromomethylidene]-7H-indolizine;

1-oxo-2,3-dianisyl-7-{1-chloro-1-{2-[4-(1-naphthyl)-6-trichloromethyl-1,3,5-triazinyl]}methylidene}-7H-indolizine; and 1-oxo-2,3-dianisyl-7-[1-bromo-1-(2-quinolinyl)methylidene]-7H-indolizine.

Each of the above mixed dyes has the same $\lambda_{max}$ and color as its 4-methoxyphenyl counterpart noted in Table I.

The cyclopropenones used in the invention having a $\lambda_{max}$ that is below 175 nm, for example, cyclopropenones bearing n-propyl substituents, are useful in the imaging elements described hereinafter, provided that the radiation source used to expose the element contains a high proportion of UV radiation and uses quartz optics or the like to transmit the UV radiation. For example, undoped mercury arc lamps are useful in such cases.

The dye of the invention is prepared by reacting the cyclopropenone and the multi-halogenated compound in an excess of pyridine. "Excess" as used herein means an amount greater than equimolar amounts. It is believed that the pyridine first reacts with the cyclopropenone, followed by a double elimination reaction with the multi-halogenated compound. This reaction does not require oxygen.

Preferably the cyclopropenone and the multi-halogenated compound are present in equimolar amounts.

The following preparations further illustrate the solution preparation of the dyes of the invention. The heating steps described are optional, being particularly useful to hasten dye development. However, heating is not required to obtain the dye. This is true particularly of dye formation in an imaging element, examples of which occur hereinafter.

Preparation 1. Synthesis of
1-oxo-2,3-di(4-methoxyphenyl)-7-{bromo-[2-(4-methyl-6-tribromomethyl-1,3,5-triazinyl)]methylidene}-7H-indolizine A solution of equimolar portions of 2,4-bis-(tribromomethyl)-6-methyl-1,3,5-triazine and 2,3-bis-(4-methoxyphenyl)cyclopropenone in excess pyridine was heated at 100° C. in air with rapid stirring. The resulting brilliant cyan solution was flooded with excess cyclohexane and filtered to furnish crude dye in 80% yield. Purification was accomplished by chromatography on silica gel to furnish the title compound, $\lambda_{max}=630$ nm.

A duplicate preparation is achievable by heating in an inert atmosphere.

Preparation 2. Synthesis of
3-oxo-1,2-diphenyl-7-{1-bromo-1-[2-(4-methyl-6-tribromomethyl-1,3,5-triazinyl)]methylidene}-7H-indolizine An equimolar solution of 2,3-diphenylcyclopropenone and 2,4-bis(tribromomethyl)-6-methyl-1,3,5-triazine in excess pyridine was boiled with stirring in air for ten minutes. The resulting deep red solution was flooded with cyclohexane and filtered to furnish the crude dye. Purification was effected by chromatography on silica gel to furnish a purified sample, $\lambda_{max}=520$ nm.

Preparation 3. Synthesis of
3-oxo-1,2-diphenyl-7-[1-bromo-1-(2-quinoxalinyl)methylidene]-7H-indolizine A solution of one equivalent of 2,3-diphenyl cyclopropenone and two equivalents of 2-tribromomethylquinoxaline in pyridine were heated on a steam bath for five minutes, flooded with cyclohexane and filtered to furnish the crude dye. Chromatography on silica gel furnished a purified sample, $\lambda_{max}=500$ nm. A minor product of the reaction obtained from the chromatography was 1-oxo-2,3-diphenyl-7-[bromo(2-quinoxylinyl)-methylidene]-7H-indolizine, $\lambda_{max}=600$ nm.

Preparation 4. Synthesis of
7-[1-bromo-1-(2-quinolinyl)methylidene]-2,3-(4-methoxyphenyl)-1(7H)-indolizinone A solution of one equivalent of 2,3-di(4-methoxyphenyl)cyclopropenone and two equivalents of 2-tribromomethylquinoline in pyridine was heated on the steam bath for 5 minutes and flooded with cyclohexane.

The resulting blue solid was chromatographed on silica gel to furnish pure product, $\lambda_{max}=600$ nm.

Preparation 5. Synthesis of
7-(1-chloro-1-cyanomethylidene)-2,3-di(4-methoxyphenyl-1(7H)-indolizinone A solution of 0.27 g (1 mmole) of 2,3-di(4-methoxyphenyl)cyclopropenone and 0.15 g (1 mmole) of trichloroacetonitrile in 10 ml of pyridine was warmed on a steam bath for 15 minutes. The solution was poured into cyclohexane and filtered. Evaporation of the cyclohexane furnished 0.25 g (50% yield) of crude product which was purified by chromatography on silica gel, $\lambda_{max}=580$ nm. The structure was confirmed by nmr and mass spectroscopic analysis.

Preparations 6-8

Compounds 6-8 identified below were prepared as follows:

A solution of 1 mmole of the halogenated starting material listed below and 1 mmole of di(4-methoxyphenyl) (or di-n-propyl) cyclopropenone in 15 ml of pyridine was heated for 15 min. on a steam bath. The reaction mixture was poured into cyclohexane, and the resulting solid water washed and chromatographed on silica gel for purification.

| No. | Compound | Halogenated Starting Material | $\lambda_{max}$ |
|---|---|---|---|
| 6 | 1-oxo-2,3-di(4-methoxyphenyl)-7-(1-aminocarbonyl-1-benzenesulfonylmethylidene)-(7H)—indolizine | 1,1-dibromo-1-phenylsulfonyl acetamide | 570 nm |
| 7 | 1-oxo-2,3-di(4-methoxyphenyl)-7-(2,4-diphenyl-1-nitro-4-oxobutylidene)-7H—indolizine | 4,4-dibromo-1,3-diphenyl-4-nitro-2-butanone | 610 nm |
| 8 | 7-[1-bromo-1-(4-tribromomethyl-6-methyl-1,3,5-triazinyl)methylidene] 2,3-di-n-propyl-1(7H)—indolizinone | 2,6-bis(tribromomethyl)-4-methyl-1,3,5-triazine | 600 nm |

All of the dyes of the preceding preparations had an optical density, after less than 1 hour, that exceeded 0.5 when measured at $\lambda_{max}$ in a cell having a 1 mm path length.

Preparations 9-10

A solution of 1 mmole of the halogenated compound noted below in Table II and 0.2 mmole of the noted cyclopropenone were added to 5 g of pyridine, and the mixture was heated to about 80° C. The noted dyes were formed after less than 1 hour, with an optical density of about 0.8 for Preparation 9 and 1.1 for Preparation 10, when measured at $\lambda_{max}$ in a 1 mm path length cell.

TABLE II

| Prep. No. | Halogenated Compound | Cyclopropenone | Dye |
|---|---|---|---|
| 9 | 4-dibromomethyl-1-carboethoxy benzene | di-4-methoxyphenylcyclopropenone | 7-[1-(4-carboethoxyphenyl)-methylidene]-2,3-di(4-methoxyphenyl)-1(7H)indolizinone |
| 10 | 1,1-dibromo-1- | di-4-methoxy- | 7-(1-aminocar |

TABLE II-continued

| Prep. No. | Halogenated Compound | Cyclo-propenone | Dye |
|---|---|---|---|
| | phenylsulfonyl acetamide | phenylcyclo-propenone | bonyl-1-benzene-sulfonylmethyli-dene)-2,3-di-(4-methoxyphenyl)-1-(7H)—indolizinone |

Preparation 11. Synthesis of Dye from a Dihalogenated Compound Having Identical $R^3$ & $R^4$ Moieties, 7-(1,1-dicyanomethylidene-2,3-di-4-methoxyphenyl-1(7H)-indolizinone The synthesis of Preparation 4 was repeated, except that dichloromalonoitrtile was used in place of 2-tribromomethylquinoline to furnish the product, $\lambda_{max} = 565$ nm.

The dyes of this invention are useful in non-image applications, for example, in dyeing fabrics and other materials. For such utility, any convenient synthesis route in addition to those just described, is also useful. For example, an intermediate reaction product produced by pyridine and a cyclopropenone will react with compound 2a or 2b to produce the dye.

A highly preferred application of this invention involves imagewise formation of the dyes in an imaging element. In such embodiments, the composition comprising cyclopropenone compound 1 and either compound 2a or 2b are applied in admixture onto a support, such as in a layer on the support. The element is dried and then exposed imagewise to activating radiation. Where exposed, the cyclopropenone decomposes and no dye is producible thereafter in those portions. The image is then developed by adding excess pyridine, which in the unexposed portions causes the dye reactions described above to take place. Optionally, and depending upon the binder of the layer, if any, the decomposition of the cyclopropenone can be used to form vesicular bubbles, as described in U.S. Pat. No. 4,128,422, issued on Dec. 5, 1978.

The excess pyridine is optionally heated to increase the rate of development. Such pyridine is either in solution form, into which the exposed element is submerged, or it is in vapor form, preferably saturated. Alternatively, the pyridine is incorporated into a layer comprising a weakly acidic polymer, and released by heating. One example of such polymers is poly(acrylic acid).

Any conventional photographic support is useful in preparing the imaging element. Useful supports include polymeric film; wood fiber, e.g., paper; metallic sheet and foil; glass; and ceramic supporting elements optionally provided with one or more subbing layers to enhance the adhesive, antistatic, dimensional, abrasive, hardness, frictional, and/or other properties of the support surface which might be desired.

Useful polymeric film supports include films of cellulose nitrate and cellulose esters such as cellulose triacetate and diacetate, polystyrene, polyamides, homo- and copolymers of vinyl chloride, poly(vinyl acetal), polycarbonate, homo- and copolymers of olefins, such as polyethylene and polypropylene, and polyesters of dibasic aromatic caarboxylic acids with divalent alcohols, such as poly(ethylene terephthalate).

Useful paper supports include those which are partially acetylated or coated with baryta and/or a polyolefin, particularly a polymer of an α-olefin containing 2 to 10 carbon atoms, such as polyethylene, polypropylene, copolymers of ethylene and propylene and the like.

Further details of useful supports are found in *Research Disclosure*, Vol. 176, Publication No. 17643, Para. XVII (December 1978), published by Industrial Opportunities Ltd., Homewell, Havant, Hampshire, PO9 1EF, United Kingdom, the contents of which is expressly incorporated herein by reference.

The imaging composition is coated onto the support using appropriate solvents. Useful coating techniques include spray-coating, whirler-coating, curtain-coating, and roll-coating, all of which are conventional. The choice of solvent depends upon the ingredients of the composition. Useful examples of solvents include acetone and toluene in admixture, cyclohexanone, and 2-ethoxyethanol.

The useful amounts of cyclopropenone and multi-halogenated compound vary, depending upon the desired result and the compounds selected. Preferably, for an imaging element, the composition is selected so that each of the cyclopropenone and multi-halogenated compound is present in an amount between about 0.01 and about 0.10 mmoles/dm$^2$ of coating. Most preferably, the amounts are about 0.05 mmoles/dm$^2$ of cyclopropenone, and between about 0.05 and 0.1 mmoles/dm$^2$ of multi-halogenated compound.

The preferred imaging elements of the invention include a binder, as described above. Alternatively, the element is useful if the support is a bibulous or fibrous support, such as filter paper, in which case the binder is omitted.

In those instances in which a binder is used, any conventional organic-solvent soluble binder is useful. For example, natural and synthetic organic polymers known to be useful binders for any kind of photographic imaging element, are useful in this invention. These include vinyl polymers such as poly(vinyl acetate), poly(vinylidene chloride), a poly(vinyl acetal) such as poly(vinyl butyral), poly(vinyl chloride-co-vinyl acetate), polystyrene, and polymers of alkyl acrylates and methacrylates including copolymers incorporating acrylic or methacrylic acid; and polyesters, such as poly(ethylene glycol-co-isophthalic acid-co-terephthalic acid), poly(p-cyclohexane dicarboxylic acid-co-isophthalic acid-co-cyclohexylenebismethanol), poly(p-cyclohexanedicarboxylic acid-co-2,2,4,4-tetrametylcyclobutane-1,3-diol) and the like. The condensation product of epichlorohydrin and bisphenol is also a useful binder.

EXAMPLES

The following examples of imaging elements further illustrate the nature of the invention.

Example 1

One gram of poly(vinyl butyral) obtained from Monsanto Chemical under the trade name Butvar 76 was dissolved in 4.5 g of acetone and 4.5 g of toluene. A brilliant clear solution was formed by stirring at room temperature. One hundred milligrams of 1,2-diphenylcyclopropenone and 300 mg of 2,4-bis(tribromomethyl)-6-methyl-1,3,5-triazine was dissolved in the dope by stirring at room temperature. The dope was coated on a 100 micron poly(ethylene terephthalate) support to a wet laydown of 150 microns. The coating was dried by heating in a stream of warm air to about 24° C. for 5 min. The clear coating was exposed imagewise through a direct-positive test pattern, to a 150 W undoped mercury arc lamp for 18 sec at a distance of about 9 cm. In the exposed area the diphenylcyclopropenone was decomposed to colorless diphenylacetylene. The image was developed by wetting the coating with a solution of 30% pyridine in a 50/50 (volume/volume) mixture of hexane and xylene. The triazine dye developed rapidly in the unexposed area to $D_{max}=1.50$, $D_{min}=0.09$. In the exposed area no color was formed.

Examples 2–5

The procedure of Example 1 was repeated, except that the cyclopropenone was dianisylcyclopropenone, Examples 2 and 3; diphenylcyclopropenone, Example 4; and dipropylcyclopropenone, Example 5; and the halogenated compounds were those listed for Preparations 4, 6, 7 and 8, respectively, described above. Equimolar amounts of the cyclopropenone and halogenated compounds were used. The dyes were obtained in the unexposed areas when the pyridine was added, producing the photographic properties of Table III below.

TABLE III

| Example | Dye | $D_{max}$ | $D_{min}$ |
|---|---|---|---|
| 2 | 7-[1-bromo-1-(2-quinolinyl)-methylidene]-2,3-dianisyl-1(7H)—indolizinone | 1.4 | 0.1 |
| 3 | 7-(1-amino-carbonyl-1-benzenesulfonylmethylidene)-2,3-dianisyl-1(7H)—indolizinone | 1.1 | 0.1 |
| 4 | Prep. 7 | 1.9 | 0.1 |
| 5 | Prep. 8 | 1.4 | 1.3 |

The high $D_{min}$ result for Example 5 is due to the fact that dipropylcyclopropeneone requires activating radiation below 200 nm to decompose. The exposure device used in the procedure of Example 1 was deficient in these wavelengths.

The invention has been described in detail with particular reference to preferred embodiments thereof, but it will be understood that variations and modifications can be effected within the spirit and scope of the invention.

What is claimed is:

1. A composition reactable with pyridine to form a dye, said composition comprising
a cyclopropenone having the structural formula

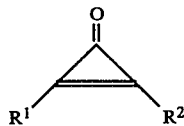

and either a compound having the structural formula

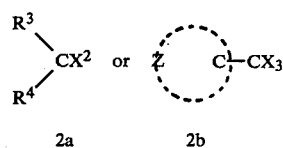

wherein $R^1$ and $R^2$ are individually alkyl of 1 to 5 carbon atoms, aryl of 6 to 10 nuclear carbon atoms, or a heterocyclic group of from 5 to 6 nuclear atoms selected from the group consisting of carbon, oxygen, and sulfur;

$R^3$ is selected from the group consisting of aryl of 6 to 10 nuclear carbon atoms and bearing a bathochromic substituent; nitro; carbonyl; amide; sulfonyl; and cyano;

$R^4$ is hydrogen, alkyl of 1 to 5 carbon atoms, halogen, or one of the group of $R^3$;

X is halogen;

and Z represents the non-metallic atoms necessary to complete one, two or three fused rings of 5 to 14 nuclear atoms selected from the group consisting of carbon and nitrogen.

2. A composition comprising
a cyclopropenone having the structural formula

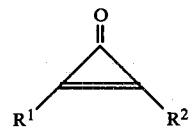

and either a compound having the structural formula

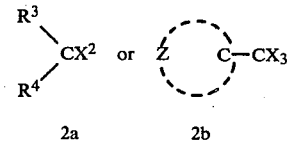

wherein $R^1$ and $R^2$ are individually alkyl of 1 to 5 carbon atoms, aryl of 6 to 10 nuclear carbon atoms, or a heterocyclic group of from 5 to 6 nuclear atoms selected from the group consisting of carbon, oxygen, and sulfur;

$R^3$ is an organic moiety such that, when 1 mmole of compound 2a is added to 5 g of pyridine as solvent and 0.2 mmole of cyclopropenone, and heated to a temperature of about 80° C. for up to 1 hour, a dye is formed having an optical density of at least 0.5 when measured at $\lambda_{max}$ in a cell having a 1 mm path length;

$R^4$ is hydrogen, alkyl of 1 to 5 carbon atoms, halogen or one of the group of $R^3$;

X is halogen;

and Z represents the non-metallic atoms necessary to complete one, two or three fused rings of 5 to 14 nuclear atoms selected from the group consisting of carbon and nitrogen.

3. A composition as defined in claim 1 or 2, wherein compound 1 is an anisyl-, phenyl- or n-propylcyclopropeneone.

4. A composition as defined in claim 1 or 2, wherein said compound 2b is present and is an azine compound, or a ring compound containing a single nitrogen atom.

5. A composition as defined in claim 4, wherein said compound 2b is an s-triazine.

6. A composition reactable with pyridine to form a dye, said composition comprising
a cyclopropenone, and
a compound containing two or three halogens that are (a) bonded to an active carbon atom and (b) reactable in pyridine with the cyclopropenone to form an indolizinone dye.

* * * * *